(12) United States Patent
Nöcker et al.

(10) Patent No.: US 11,110,041 B2
(45) Date of Patent: Sep. 7, 2021

(54) PROCESS FOR PERMANENT SHAPING HAIR

(71) Applicant: KAO GERMANY GMBH, Darmstadt (DE)

(72) Inventors: Bernd Nöcker, Darmstadt (DE); Steven Breakspear, Darmstadt (DE); Peter Bauer, Darmstadt (DE); Jonathan Wood, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 378 days.

(21) Appl. No.: 15/757,839

(22) PCT Filed: Mar. 15, 2016

(86) PCT No.: PCT/EP2016/055584
§ 371 (c)(1),
(2) Date: Mar. 6, 2018

(87) PCT Pub. No.: WO2017/041905
PCT Pub. Date: Mar. 16, 2017

(65) Prior Publication Data
US 2018/0338893 A1 Nov. 29, 2018

(30) Foreign Application Priority Data
Sep. 8, 2015 (EP) .................... 15184311

(51) Int. Cl.
| | | |
|---|---|---|
| *A61K 8/19* | (2006.01) | |
| *A61Q 5/04* | (2006.01) | |
| *A61K 8/23* | (2006.01) | |
| *A45D 7/04* | (2006.01) | |
| *A61K 8/22* | (2006.01) | |
| *A61K 8/362* | (2006.01) | |
| *A61K 8/365* | (2006.01) | |
| *A61K 8/44* | (2006.01) | |
| *A61K 8/20* | (2006.01) | |

(52) U.S. Cl.
CPC .............. *A61K 8/19* (2013.01); *A45D 7/04* (2013.01); *A61K 8/20* (2013.01); *A61K 8/22* (2013.01); *A61K 8/23* (2013.01); *A61K 8/362* (2013.01); *A61K 8/365* (2013.01); *A61K 8/44* (2013.01); *A61Q 5/04* (2013.01)

(58) Field of Classification Search
None
See application file for complete search history.

(56) References Cited

U.S. PATENT DOCUMENTS

| | | | |
|---|---|---|---|
| 2012/0230935 A1* | 9/2012 | Kim ................... | A61K 8/46 424/70.51 |
| 2012/0234339 A1* | 9/2012 | Hullmann ............. | A61K 8/23 132/205 |
| 2015/0034119 A1 | 2/2015 | Pressly et al. | |
| 2015/0037270 A1 | 2/2015 | Pressly et al. | |

FOREIGN PATENT DOCUMENTS

| | | |
|---|---|---|
| EP | 2 332 515 A1 | 6/2011 |
| EP | 2 338 471 A1 | 6/2011 |
| EP | 2 468 250 A1 | 6/2012 |
| WO | 2015/017768 A1 | 2/2015 |

OTHER PUBLICATIONS

International Search Report dated Apr. 25, 2016, dated May 13, 2016.

* cited by examiner

*Primary Examiner* — Nicole P Babson
(74) *Attorney, Agent, or Firm* — Norris McLaughlin, P.A.

(57) ABSTRACT

The present invention relates to a process for improved and milder permanent shaping of hair, especially human hair. It has been found that when commonly used permanent shaping compositions are mixed with another composition comprising predominantly carboxylic acids, the permanent shaping effect of the composition is improved, homogeneous permanent shaping of hair fibers is achieved and natural cosmetic properties of hair are maintained.

16 Claims, No Drawings

PROCESS FOR PERMANENT SHAPING HAIR

This application is the U.S. National Stage of International Application No. PCT/EP2016/055584, filed Mar. 15, 2016, which claims foreign priority benefit under 35 U.S.C. § 119 of European Application No. 15184311.7 filed Sep. 8, 2015 the disclosures of which are incorporated herein by reference.

The present invention relates to a permanent shaping process for improved and milder shaping of hair, especially human hair.

Permanent shaping of hair involves application of a strong reductive composition onto hair and leaving it for a certain period of time, usually at elevated temperatures, in order to open up the disulfide bonds and rebuilding them in the preferred shape with an application of an oxidative composition. Since the process involves the use of strong reductive and oxidative compositions, the hair fiber itself is affected by such treatment and therefore it also loses its certain natural properties such as its strength against breaking, its natural elasticity, its natural shine and natural soft feel upon touching.

Moreover, the to be permanently shaped hair is not always homogeneous in its physicochemical status as it may be damaged due to previous chemical treatments such as dyeing and permanently shaping and/or environmental effects. This often leads to inhomogeneous permanent shaping performance and therefore often consumers' dissatisfaction. There is, therefore, a great need for milder and more effective permanent shaping compositions which overcome one or more of the above mentioned problems.

Recently in a series of patent applications (US2015/0034119, US2015/0037270, WO2015/017768) methods are published which claim benefits of the combined use of a bismaleate based binding agent in hair chemical treatments such as oxidative hair dyeing, permanently shaping and bleaching for improving hair structure. The publications are silent on the core of the present invention.

After a long research and careful considerations of the consumers' needs, the inventors of the present invention have unexpectedly found out that when commonly used permanent shaping compositions are mixed with another composition comprising predominantly carboxylic acids, the permanent shaping effect of the composition is improved, homogeneous permanent shaping of hair fibers is achieved and natural cosmetic properties of hair are maintained.

Therefore, the first object of the present invention is a process for permanent shaping hair, especially human hair, comprising the following steps
- a—optionally washing the hair with a cleansing composition and towel drying,
- b—applying the ready-to-use composition obtained by mixing the compositions A and B immediately before application onto hair at a weight ratio of A to B in the range of 10:0.1 to 10:1, and leaving it on the hair for 1 to 45 min,
- c—optionally rinsing-off the hair with water,
- d—optionally applying an intermediate treatment composition comprising one or more inorganic salts and having a pH from 2 to 7,
- e—applying a fixing composition comprising one or more oxidizing agents, preferably hydrogen peroxide, and having a pH in the range of 1.5 to 5 and leaving it on the hair for 1 to 15 min,
- f—optionally rinsing off from hair,
- g—optionally drying, wherein the composition A is an aqueous composition comprising one or more reducing agents, one or more alkalizing agents and has a pH in the range of 7.5 to 12, and
wherein the composition B comprises
i) one or more carboxylic acids having three or more carboxyl groups and/or their salts, and
ii) one or more additional organic acid and/or their salts having one or two carboxyl groups,
wherein the composition B comprises the acids of i) and ii) and/or their salts at a total concentration from 10% to 100% by weight, calculated to the total of the composition B,
wherein the ready-to-use composition has an alkaline pH in the range from 7.3 to 11 and comprises the acids and/or their salts at a total concentration in the range of 1% to 10% by weight, calculated to the total of the ready-to-use composition,
wherein the hair is put under tension before, during or after application of the ready to use composition, and wherein the tension is released from hair before or during application of the fixing composition or prior to rinsing off the oxidizing agent form hair.

In a preferred embodiment of the present invention the hair is put under tension before application of the reducing agent onto hair and the tension is released from hair after rinsing off the oxidizing agent from hair.

The second object is a kit for hair, especially human hair, comprising the compositions A and B of the present invention, a third aqueous composition comprising an oxidizing agent, preferably hydrogen peroxide, and having a pH in the range of 1.5 to 5 and optionally another composition comprising one or more inorganic salts and has a pH in the range of 2 to 7.

The composition A comprises one or more reducing agents. Useful are thioglycolic acid and/or its salts, cysteamine and/or its salts, thioglycerin and/or its salts, glycerin esters of thioglycolic acid and/or its salts, thiolactic acid and/or its salts, cysteine or its derivatives and/or its salts and sodium sulfite. Preferred are thioglycolic acid and/or its salts, thiolactic acid and/or its salts, and cysteine or its derivatives and/or its salts. The most preferred is thioglycolic acid and/or its salts.

One or more reducing agents are comprised in the composition A at a concentration in the range of 1% to 15%, preferably 2% to 15%, more preferably 3% to 12.5% and most preferably 5% to 11% by weight calculated to the total of composition A.

The composition A comprises one or more alkalizing agents. Suitable ones are ammonia and alkyl- or alkanolamines according to the general structure

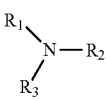

wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_1$, $R_2$, or $R_3$ is different from H, wherein the alkalizing agents preferably selected from ammonia, monoethanolamine, and aminomethyl-propanol, and particularly suitable one is aminomethyl-propanol.

The alkalizing agent is comprised in the composition A at a total concentration of 1% to 20%, preferably 1% to 17.5%, more preferably 2% to 15% and most preferably 2.5% to 13% by weight calculated to the total of the composition A.

The composition A has a pH in the range of 7.5 to 12, preferably 8 to 11, and more preferably 8.5 to 10.5 and most preferably 8 to 10 measured at 20° C.

The composition B comprises
i—one or more carboxylic acids having three or more carboxyl groups and/or their salts, and
ii—one or more additional organic acid and/or their salts having one or two carboxyl groups.

Suitable carboxylic acids with three or more carboxyl groups and/or their salts are citric acid, ethylenediamine tetraacetic acid (EDTA), pyromellitic acid and glutamate diacetate. The ethylenediamine tetraacetic acid (EDTA) and/or its salts such as monosodium, disodium, trisodium and tetrasodium salts are the most preferred ones.

Suitable organic acids with one or two carboxyl groups and/or their salts are acetic acid, malic acid, lactic acid, glycolic acid, tartaric acid, formic acid, oxalic acid, malonic acid, succinic acid, glutaric acid, adipic acid, maleic acid, and fumaric acid. In the preferred embodiment of the present invention the composition B comprises as the second acid one or more organic acids having one or two carboxyl groups and the most preferred acid is malic acid and/or its salts such as sodium, potassium and ammonium salts.

The composition B comprises the two acids and/or their salts at a total concentration in the range of 10% to 100% by weight, preferably 12.5% to 90%, more preferably 12.5% to 75% by weight and most preferably 12.5% to 60% by weight, calculated to the total of composition B.

The two acids are comprised in the composition B at a weight ratio of first acid (i) to second acid (ii) in the range from 10:1 to 1:250, preferably from 5:1 to 1:150, and more preferably from 2:1 to 1:100 and most preferably 1:50.

The composition B may be in the form of a powder, a dispersion, an emulsion or a solution. In a preferred embodiment of the present invention the composition B is an aqueous composition and preferably has a pH in the range of 1 to 5, preferably 2 to 4, more preferably in the range of 2.5 to 3.6. In the case that the pH must be adjusted to a certain value, the composition B may comprise one or more alkalizing agents as disclosed above for the composition A. The preferred are ammonia, monoethanolamine, and aminomethyl-propanol and the aminomethyl-propanol is particularly preferred.

The alkalizing agent is comprised in the composition B at a total concentration of 1% to 20%, preferably 1% to 17.5%, more preferably 2% to 15% and most preferably 2.5% to 13% by weight calculated to the total of the composition B.

In a further preferred embodiment of the present invention, the composition B comprises one or more thickening polymers selected from anionic, nonionic, cationic and amphoteric polymers, preferably selected from polymers with a viscosity of at least 500 mPa·s measured at a polymer concentration of 1% by weight in water and at 20° C. with a Brookfield viscometer, such as at 10 rpm for 1 minute, with an appropriate spindle.

Suitable polymers are cellulose polymers, alginates, polysaccharides and acrylic acid polymers, preferably methyl cellulose, ethyl cellulose, hydroxyethylcellulose, methylhydroxyethylcellulose, methylhydroxypropylcellulose, carboxymethyl cellulose, alginic acids, sodium alginates, ammonium alginates, calcium alginates, gum arabic, guar gum or xanthan gum, dehydroxanthan gum or acrylic acid polymers known with the CTFA adopted name Carbomer and its derivatives.

The preferred polymers are dehydroxanthan gum, xanthan gum, and polymeric anionic thickeners Carbomer and its derivatives. The particularly preferred thickening agent is dehydroxanthan gum. The thickening agents are preferably comprised in the composition B at a total concentration in the range of 0.1% to 5%, preferably, 0.2% to 3%, more preferably 0.25% to 2.5% and most preferably 0.3% to 2% by weight calculated to the total of the composition B.

The pH of the ready-to-use composition obtained by mixing the composition A and B, is in the range of 7.3 to 11, preferably 7.5 to 10.5, more preferably 7.8 to 10 measured at 20° C.

Any of the compositions A and/or B may comprise one or more of the commonly used hair conditioning compounds. These compounds are for example fatty alcohols, surfactants such as anionic, nonionic, cationic and amphoteric ones, ubiquinones, ceramides, organic solvents, lipophilic ingredients such as vegetable oils, mineral oils, silicones, fatty acid fatty alcohol esters, preservatives, amino acids, and polyols. It should be noted that these compounds are optionally comprised in the any of the compositions and their incompatibility must be carefully considered prior to addition in the compositions.

Any of the composition may comprise one or more fatty alcohols. In particular the compositions A and/or B may be aqueous compositions and may further be in the form of an emulsion and then comprise preferably one or more fatty alcohols. Suitable fatty alcohols are the ones with the chain length of 14 to 22 C atoms which may be saturated or unsaturated, linear or branched which may as well be substituted. Non-limiting examples are myristyl alcohol, cetyl alcohol, stearyl alcohol, behenyl alcohol and cetostearyl alcohol.

The total concentration of fatty alcohol is in the range from 0.1% to 20%, preferably 0.5% to 15%, more preferably 1% to 10% by weight, calculated to the total of each composition.

Compositions A and B according to the present invention may comprise surfactants selected from anionic, nonionic, amphoteric and/or cationic surfactants. The anionic, nonionic, amphoteric surfactants are used generally as emulsifier or solubilizer whereas the cationic surfactants are at the same time particularly used as hair conditioners.

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

Further surfactants suitable are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "Pluronics$^R$", as well as fatty alcohol ethoxylates, $C_{22}$-fatty alcohol ethoxylates, known by the generic terms "Laureth", "Mysristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Suitable cationic surfactants are according to the general structure

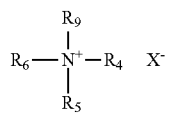

where $R_5$ is a saturated or unsaturated, branched or linear alkyl chain with 8-22 C atoms or

where $R_7$ is saturated or unsaturated, branched or linear alkyl chain with 7-21 C atoms and n has typical value of 1-4 or

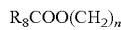

where $R_8$ is saturated or unsaturated, branched or linear alkyl chain with 7-21 C atoms and n has typical value of 1-4, and $R_4$ is H or unsaturated or saturated, branched or linear alkyl chain with 1-22 C atoms or

or

where $R_7$, $R_8$ and n are same as above.

$R_9$ and $R_6$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Concentration of one or more total surfactants in any of the compositions A and/or B is in the range of 0.1% to 20%, preferably 0.2% to 15% and most preferably 0.2% to 10% by weight, calculated to the total of each composition.

The compositions A, and/or B may further comprise lipophilic ingredients such as vegetable oils, for example, jojoba oil or any other; liquid paraffins, especially paraffinum perliquidum and paraffinum subliquidurn, silicones for example linear polysiloxanes such as dimethicones with various consistency and dimethiconols, aminated silicones with primary, secondary, tertiary or quaternary ammonium groups such as amodimethicone, polysilicone 9, and quaternium 80, cyclic silicones such as cyclomethicones, arylated silicones such as phenyl trimethicone; fatty acid esters such as octyl palmitate, isocetyl palmitate, isopropyl palmitate and octyl stearate, $C_{10}$- to $C_{36}$-fatty acid triglycerides, as well as their mixtures. Total concentration of these lipophilic compounds is in the range of 0.1% to 20% by weight, preferably from 1% to 15% by weight, and more preferably from 2% to 10% by weight, calculated to the total of each composition.

Composition A and/or B can also comprise cationic polymers as conditioning and/or thickening agents. Those are cationic cellulose type polymers know as Polymer JR type from Amerchol such as Polyquaternium 10 or cationic guar gum known with trade name Jaguar from Rhone-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

Equally suitable are those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

The total concentration of cationic polymers may be in the range of 0.1% to 7.5% by weight, preferably 0.3% to 5% by weight and more preferably 0.5% to 2.5% by weight, calculated to the total of each composition.

Composition A and/or B may comprise one or more ceramide compound, such as the one according to general formula

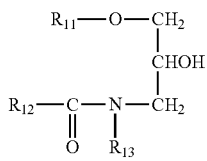

where $R_{11}$ and $R_{12}$ are independent from each other an alkyl- or alkenyl group with 10 to 22 carbon atoms, $R_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01% to 2%, preferably 0.01% to 1% by weight calculated to the total or each composition.

The compositions A and/or B may comprise ubiquinone of the formula:

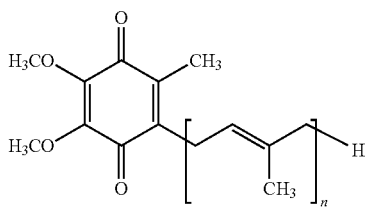

wherein n is a number from 1 to 10. The concentration of ubiquinone can vary between 0.001% and 10% by weight, calculated to the total of each composition.

The compositions A and/or B may comprise one or more organic solvents such as 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol. The concentration of one or more organic solvents is in the range of 0.1% to 15%, preferably 0.5% to 12.5% and more preferably 1% to 10% and most preferably 1% to 7.5% by weight calculated to the total of each composition.

The compositions A and/or B may further comprise one or more amino acids, preferably at a concentration in the range of 0.01% to 5%, preferably 0.1% to 3% and more preferably 0.2% to 2.5% and most preferably 0.25% to 2% by weight calculated to the total of each composition. Suitable ones are all of the known amino acids such as, arginine, alanine, asparagine, glutamine, glycine, histidine, leucine, lysine, methionine, phenylalanine, proline, serine, threonine, tryptophan, tyrosine and valine.

The compositions A and/or B may further comprise one or more polyols, preferably at a concentration in the range of 0.01% to 5%, preferably 0.1% to 3% and more preferably 0.2% to 2.5% and most preferably 0.25% to 2% by weight calculated to the total of each composition. Suitable ones are propylene glycol, dipropylene glycol, glycerine, panthenol and its derivatives.

The compositions A and/or B may further comprise any known preservatives if necessary.

The oxidizing composition used in the process for permanent shaping hair for rebuilding the disulfide bonds is an aqueous composition and comprises one or more oxidizing agent(s). The suitable oxidizing agents are hydrogen peroxide, urea peroxide, melamin peroxide, and perborate salts. The most preferred one is hydrogen peroxide. The oxidizing composition comprises one or more oxidizing agents at a total concentration of 0.2% to 5% by weight, preferably 0.5% to 4%, more preferably 1% to 3.5% and most preferably 1% to 2.5% by weight, calculated to the total of the oxidizing composition. The pH of the oxidizing composition is in the range from 1.5 to 5.

In the permanently shaping process an aqueous intermediate treatment composition may preferably be used in order to de-swell hair for minimizing further damage to the hair fibre after rinsing off the reducing composition. The intermediate composition is applied onto hair after rinsing off the reducing composition but before applying the oxidizing composition and preferably left on the hair up to 15 min, more preferably up to 10 min and optionally rinsed off from hair prior to application of oxidizing composition. The intermediate composition comprises one or more inorganic salts, preferably at a concentration of 0.5% to 15%, more preferably 1% to 12.5% and most preferably 2% to 12.5% by weight calculated to the total composition.

In principle any water soluble inorganic salt is suitable for the purpose. In the preferred embodiment, salts are preferably selected from salts of mono or divalent cations with mono and divalent anions. Preferred cations are sodium, calcium, potassium and magnesium and anions are chloride and sulfate. Suitable ones are such as sodium chloride, sodium sulfate, magnesium sulfate, potassium chloride, potassium sulfate, magnesium chloride, calcium chloride, ammonium salts such as ammonium chloride and ammonium sulfate. Additionally special salts are found suitable such as of iodide ions, especially potassium and sodium salts, copper chloride, copper sulfate, cobalt chloride, cerium sulfate, cerium chloride, vanadium sulfate, lithium chloride, magnesium acetate, calcium nitrate, barium nitrate, magnesium oxide, and ammonium nitrate. Preferred inorganic salts are sodium chloride, sodium sulfate, magnesium sulfate, potassium chloride, potassium sulfate, magnesium chloride, calcium chloride and salts of iodide ions. More preferably the salts are sodium chloride, sodium sulfate, magnesium sulfate, potassium chloride, potassium sulfate, magnesium chloride and salts of iodide ions especially potassium and sodium salts. In particular, with magnesium sulfate, sodium chloride and potassium iodide exceptionally good results are observed.

The total concentration of one or more inorganic salts in the aqueous intermediate composition is typically from 0.01% to 20%, preferably 0.05% to 15% and most preferably 0.1% to 10% and in particular 0.2% to 7.5% by weight calculated to the total of the intermediate composition.

The intermediate treatment composition may preferably comprise an oxidizing agent at a concentration of 0.1% to 5%, preferably 0.2% to 5% more preferably 0.2% to 3% and most preferably 0.2% to 2% by weight calculated to the total composition. Suitable oxidizing agents are hydrogen peroxide and sodium bromate. Most preferred is hydrogen peroxide.

The intermediate treatment composition has a pH between 2 and 7, preferably 2.5 and 6 and more preferably 3 and 5.

The following examples are to illustrate the invention, but not to limit it.

EXAMPLE 1

The Composition A

| | % by weight |
|---|---|
| Ammonium thioglycolate (60%) | 21.3 |
| Ammonium hydrogen carbonate | 5.0 |
| 1,3-butylene gylcol | 3.0 |
| Amodimethicone | 0.2 |
| PEG-40-Hydrogenated castor oil | 0.7 |
| Fragrance | 0.4 |
| Ammonia, 25% | ad pH 8.3 |
| Water | ad 100.0 |

The Composition B

| | % by weight |
|---|---|
| EDTA tetrasodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition B was approximately 3.5.

Oxidizing Composition

| | % by weight |
|---|---|
| Hydrogen peroxide | 2 |
| Phosphoric acid | q.s. to pH 3.5 |
| Water | to 100 |

With the compositions of above a straight perming was conducted according to the process of the present invention. Caucasian hair of 25 cm length was obtained from Fischbach+Miller, Laupheim, Germany. The reducing composition A given above was applied onto hair after mixing with the composition B at a weight ratio of composition A to B 10:0.2 and processed for 20 minutes at room temperature. Then the composition was rinsed off from hair for 3 min and the hair was blow dried. Heat was applied to hair with a flat iron set to 180° C. with a total of three strokes per hair streak. Then the oxidizing composition C was applied and processed for 10 minutes at room temperature. The hair was then rinsed with water for 1 min (inventive process).

For comparison purposes a similar process of above was applied to hair with the exception that composition B was replaced with an equal amount of water instead of composition B (comparative process).

Evenness of perm was investigated on pre-damaged hair. Damage was conferred to hair by bleaching hair with a commercially available bleaching composition under the brand Goldwell. Then, the inventive and comparative process of above was applied to separate hair streaks and processed as described above. The result was recorded by measuring spreading of the hair streaks and calculation of a volume factor based on the spreading of hair at the root and at the tip parts. In other words, width of hair streaks were measured at their root and at their tips by placing the hair streaks on millimeter paper. A volume factor was calculated according to equation (1):

$$Volume factor = \frac{\text{Width at hair tips [cm]}}{\text{Width at hair root [cm]}} \quad \text{Equation (1)}$$

Hair streaks before treatment displayed a volume factor of 1.1. As a result of the treatment, the hair treated according to the inventive process had a volume factor of 1.33, whereas the hair treated according to the comparative process had a volume factor of 2.23. In conclusion, the comparative process led to a much higher increase of hair volume which is definitively undesired by the customer as a result of a straightening process. The inventive process did not lead to such an increase.

Damage reduction was investigated on virgin hair streaks which were processed three times with the inventive and comparative processes as described above. Stress-strain analysis was conducted with the hair streaks upon these treatments on 30 hair fibers.

| Measurement | Inventive Process | | Comparative Process | |
|---|---|---|---|---|
| number | Stress [MPa] | Strain [%] | Stress [MPa] | Strain [%] |
| 1 | 25.29 | 10 | 30.59 | 10 |
| 2 | 32.94 | 20 | 38.24 | 20 |
| 3 | 47.06 | 30 | 53.53 | 30 |
| 4 | 70.88 | 40 | 84.41 | 40 |
| 5 | 86.18 | 45 | 102.94 | 45 |

The obtained data clearly showed that the hair streaks treated with the inventive process conferred the hair a much higher elasticity compared to the comparative process. For the inventive process less stress was needed to achieve a certain strain rate. This effect sustains over all investigated strain rates. Consequently the inventive process led to hair with much more desired cosmetic properties compared to the state-of-the-art process.

EXAMPLE 2

Intermediate Composition

| | % by weight |
|---|---|
| Magnesium sulfate | 10 |
| Cetrimonium chloride | 0.5 |
| Citric acid | q.s. to pH 4.2 |
| Water | q.s. to 100 |

In the process disclosed with Example 1 above, the intermediate treatment composition was applied onto hair after treating hair with heat. The intermediate treatment composition was left on hair for 5 min and without rinsing it off, then the oxidizing composition was applied. The observed straight perming results with the Example 1 were confirmed.

Similar results were obtained with the following compositions.

EXAMPLE 3

The Composition B

| | % by weight |
|---|---|
| EDTA tetrasodium salt | 5.0 |
| Malic acid | 15.0 |

-continued

| | % by weight |
|---|---|
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition was approximately 3.6.

EXAMPLE 4

The Composition B

| Component | % by weight |
|---|---|
| AMP | 6.0 |
| EDTA tetrasodium salt | 3.0 |
| Malic acid | 13.0 |
| Lactic acid | 4.0 |
| Hydroxypropyl xanthan gum | 0.6 |
| Polyquaternium-10 | 0.1 |
| Water | to 100 |
| pH | 3.4 ± 0.1 |

EXAMPLE 5

The Composition B

| Component | % by weight |
|---|---|
| Monoethanolamine (MEA) | 2.7 |
| EDTA tetrasodium salt | 5.0 |
| Malic acid | 15.0 |
| Hydroxypropyl xanthan gum | 0.6 |
| Panthenol | 0.1 |
| Water | To 100 |
| pH | 3.3 ± 0.1 |

EXAMPLE 6

The Composition B

| Component | % by weight |
|---|---|
| AMP | 6.0 |
| Citric acid | 5.0 |
| Maleic acid | 15.0 |
| Hydroxypropyl xanthan gum | 0.6 |
| Behenamidopropyl trimonium chloride | 0.2 |
| Water | to 100 |
| pH | 1.5 ± 0.1 |

EXAMPLE 7

The Composition B

| Component | % by weight |
|---|---|
| MEA | 2.0 |
| Lactic acid | 15.0 |
| Citric acid | 6.0 |

| Component | % by weight |
|---|---|
| Hydroxypropyl xanthan gum | 0.6 |
| Polyquaternium-67 | 0.1 |
| Water | to 100 |
| pH | 2.7 ± 0.1 |

EXAMPLE 8

The Composition A

| | % by weight |
|---|---|
| Ammonium thioglycolate (60%) | 0.9 |
| Cystein hydrochloride | 5.7 |
| Ammonium hydrogen carbonate | 1.5 |
| Acetylcystein | 0.7 |
| Cetrimonium chloride | 0.1 |
| 1,3- butylene gylcol | 0.5 |
| Amodimethicone | 0.2 |
| Fragrance | 0.4 |
| Ammonia, 25% | ad pH 9.8 |
| Water | q.s. 100.0 |

The Composition B

| | % by weight |
|---|---|
| EDTA tetrasodium salt | 4.0 |
| Malic acid | 17.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition was 3.4.

EXAMPLE 9

The Composition B (Powder)

| | % by weight |
|---|---|
| EDTA tetrasodium salt | 7.0 |
| Malic acid | 93.0 |

1 g of the composition above was added to the mixture of 30 g of composition A of Example 1. After mixing thoroughly, the resulting composition was applied onto hair which was already put under tension using curlers and rinsed off after leaving it on the hair for 30 min. The hair was applied the intermediate composition of the Example 2 above and after leaving it for 5 min on the hair without rinsing off, the oxidizing composition of Example 1 was applied and the curlers were removed after processing of the oxidizing agent for 5 min which was followed by further processing for 5 min and rinsing off the hair with water. Then the hair was dried. It was observed that hair was effectively and homogeneously curled and had its natural softness and elasticity.

EXAMPLE 10

The Composition B

|  | % by weight |
| --- | --- |
| EDTA monosodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.1.

EXAMPLE 11

The Composition B

|  | % by weight |
| --- | --- |
| EDTA disodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.2.

EXAMPLE 12

The Composition B

|  | % by weight |
| --- | --- |
| EDTA trisodium salt | 1.0 |
| Malic acid | 13.0 |
| Aminomethylpropanol | 6.0 |
| Hydroxypropyl xanthan gum | 0.6 |
| Cetrimonium chloride | 0.1 |
| Preservative | q.s. |
| Water | to 100 |

The pH of the above composition D is approximately 3.4.

The invention claimed is:

1. A process for permanent shaping hair, the process comprising:
    a—optionally washing hair with a cleansing composition and towel drying the hair;
    b—mixing a composition A and a composition B immediately before application onto the hair at a weight ratio of composition A to composition B in the range of 10:0.1 to 10:1 to obtain a ready-to-use composition having an alkaline pH in the range from 7.3 to 11;
    c—applying the obtained ready-to-use composition onto the hair, and leaving the applied ready-to-use composition on the hair for 1 to 45 min;
    d—optionally rinsing the applied ready-to-use composition off the hair with water;
    e—optionally applying, onto the hair, an intermediate treatment composition comprising one or more inorganic salts and having a pH from 2 to 7;
    f—applying, onto the hair, a fixing composition comprising one or more oxidizing agents and having a pH in the range of 1.5 to 5 and leaving the applied fixing composition on the hair for 1 to 15 min;
    g—optionally rinsing the applied fixing composition off the hair; and
    h—optionally drying the hair,
    wherein
    the composition A is an aqueous composition comprising one or more reducing agents, one or more alkalizing agents, and has a pH in the range of 7.5 to 12,
    the composition B comprises;
        i) one or more carboxylic acids having three or more carboxyl groups and/or their salts; and
        ii) one or more additional organic acids and/or their salts having one or two carboxyl groups,
    the composition B comprises the acids of i) and ii) and/or their salts at a total concentration from 10% to 100% by weight, based on a total of the composition B,
    the obtained ready-to-use composition comprises the acids of i) and ii) and/or their salts at a total concentration in the range of 1% to 10% by weight, based on a total of the obtained ready-to-use composition,
    the composition B comprises the acids of (i) and (ii) at a weight ratio (i)/(ii) ranging from 10:1 to 1:250,
    the hair is put under tension before, during, or after application of the obtained ready-to-use composition, and
    the tension is released from the hair before or during application of the fixing composition or prior to rinsing off the applied fixing composition off the hair.

2. The process of claim 1, wherein the hair is put under tension before application of the obtained ready-to-use composition.

3. The process of claim 2, wherein the tension is released from the hair after rinsing off the applied fixing composition off the hair.

4. The process of claim 1, wherein
    the one or more carboxylic acids having three or more carboxyl groups are selected from citric acid, ethylene diamine tetra acetic acid (EDTA), pyromellitic acid, and glutamate diacetate, and
    the one or more additional organic acids with one or two carboxyl groups are selected from acetic acid, malic acid, lactic acid, glycolic acid, tartaric acid, formic acid, oxalic acid, malonic acid, succinic acid, glutaric acid, adipic acid, maleic acid, and fumaric acid,
    the composition B comprises the acids of (i) and (ii) at a weight ratio (i)/(ii) ranging from 5:1 to 1:150, and
    the obtained ready-to-use composition has an alkaline pH in the range from 7.5 to 10.5.

5. The process of claim 1, wherein the composition B is a powder, a dispersion, an emulsion, a solution, or an aqueous composition.

6. The process of claim 1, wherein the pH of composition B ranges from 1 to 5 and the composition B further comprises an alkalizing agent.

7. The process of claim 1, wherein the one or more carboxylic acids having three or more carboxyl groups is EDTA and/or its salts.

8. The process of claim 1, wherein the one or more organic acids having one or two carboxyl groups is malic acid and/or its salts.

9. The process of claim 1 wherein the one or more reducing agents of the composition A are selected from thioglycolic acid, cysteamine and/or its salts, thioglycerin and/or its salts, glycerin esters of thioglycolic acid and/or its salts, thiolactic acid and/or its salts, and cysteine or its derivatives and/or its salts, wherein the one or more reducing agents are present at a concentration ranging from 1 to 15% by weight, based on a total of composition A.

10. The process of claim 6, wherein at least one of the one or more alkalizing agents of the Composition A and at least one alkalizing agent of the composition B is selected from ammonia, alkyl- or alkanolamines according to the general structure

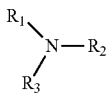

wherein $R_1$, $R_2$, and $R_3$ are same or different and are selected from H, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, and $C_3$ to $C_4$ branched hydroxyl alkyl, with the condition that at least one of $R_1$, $R_2$, or $R_3$ is different from H.

11. The process of claim 1, wherein at least one of the composition A and the composition B comprise(s) one or more ingredients selected from fatty alcohols, surfactants selected from anionic surfactants, nonionic surfactants, cationic surfactants, and amphoteric surfactants, ubiquinones, reducing agents, organic solvents, linear polysiloxanes, aminated silicones, cyclic silicones, arylated silicones, antioxidants, preservatives, amino acids, and polyols.

12. The process of claim 1, wherein the composition B comprises one or more thickening polymers selected from anionic, nonionic, cationic and amphoteric polymers, with a viscosity of at least 500 mPa·s measured at a polymer concentration of 1% by weight in water and at 20° C. with a Brookfield viscometer, with an appropriate spindle.

13. The process of claim 12, wherein the one or more thickening polymers are selected from hydroxypropyl xanthan gum, dehydroxanthan gum, xanthan gum, and polymeric anionic thickeners.

14. The process of claim 1, wherein
the one or more carboxylic acids having three or more carboxyl groups of composition B is EDTA and/or its salts, and
the one or more additional organic acids having one or two carboxyl groups is malic acid and/or its salt.

15. The process of claim 1, wherein the weight ratio (i)/(ii) ranges from 1:13 to 1:250.

16. A process for permanent shaping hair, the process comprising:
a—applying a ready-to-use composition onto the hair, wherein the ready-to-use composition is obtained by mixing a composition A and a composition B immediately before application onto the hair at a weight ratio of composition A to composition B in the range of 10:0.1 to 10:1, and leaving the applied ready-to-use composition on the hair for 1 to 45 min;
b—applying, onto the hair, a fixing composition comprising one or more oxidizing agents and having a pH in the range of 1.5 to 5 and leaving the applied fixing composition on the hair for 1 to 15 min; wherein
the composition A is an aqueous composition comprising one or more reducing agents, one or more alkalizing agents, and has a pH in the range of 7.5 to 12,
the composition B comprises;
  i) one or more carboxylic acids having three or more carboxyl groups and/or their salts selected from citric acid, ethylene diamine tetra acetic acid (EDTA), pyromellitic acid, glutamate diacetate, and their salts; and
  ii) one or more additional organic acids and/or their salts having one or two carboxyl groups selected from acetic acid, malic acid, lactic acid, glycolic acid, tartaric acid, formic acid, oxalic acid, malonic acid, succinic acid, glutaric acid, adipic acid, maleic acid, fumaric acid, and their salts,
the composition B comprises the acids of i) and ii) and/or their salts at a total concentration from 10% to 100% by weight, based on a total of the composition B,
the ready-to-use composition has an alkaline pH in the range from 7.3 to 11 and comprises the acids of i) and ii) and/or their salts at a total concentration in the range of 1% to 10% by weight, based on a total of the ready-to-use composition,
the composition B comprises the acids of (i) and (ii) at a weight ratio (i)/(ii) ranging from 10:1 to 1:250,
the hair is put under tension before, during, or after application of the ready-to-use composition, and
the tension is released from the hair before or during application of the fixing composition or prior to rinsing off the applied fixing composition off the hair.

* * * * *